(12) United States Patent
Huang et al.

(10) Patent No.: US 10,835,105 B1
(45) Date of Patent: Nov. 17, 2020

(54) DISPLAY CORRECTION SYSTEM FOR ENDOSCOPE AND THE CORRECTION METHOD THEREOF

(71) Applicant: DIVA LABORATORIES, LTD., New Taipei (TW)

(72) Inventors: Ching-Min Huang, New Taipei (TW); Chuan-Ling Peng, New Taipei (TW)

(73) Assignee: Diva Laboratories, Ltd., New Taipei (TW)

( * ) Notice: Subject to any disclaimer, the term of this patent is extended or adjusted under 35 U.S.C. 154(b) by 0 days.

(21) Appl. No.: 16/557,157

(22) Filed: Aug. 30, 2019

(30) Foreign Application Priority Data

Jun. 27, 2019 (TW) .............................. 108122644 A

(51) Int. Cl.
| | |
|---|---|
| *H04N 9/64* | (2006.01) |
| *A61B 1/273* | (2006.01) |
| *A61B 1/267* | (2006.01) |
| *A61B 1/00* | (2006.01) |
| *H04N 17/00* | (2006.01) |
| *A61B 1/045* | (2006.01) |
| *A61B 1/31* | (2006.01) |
| *A61B 1/313* | (2006.01) |
| *A61B 1/307* | (2006.01) |

(52) U.S. Cl.
CPC ...... *A61B 1/00009* (2013.01); *A61B 1/00045* (2013.01); *A61B 1/00096* (2013.01); *A61B 1/045* (2013.01); *A61B 1/2676* (2013.01); *A61B 1/2736* (2013.01); *A61B 1/307* (2013.01); *A61B 1/31* (2013.01); *A61B 1/3132* (2013.01); *H04N 9/646* (2013.01); *H04N 17/002* (2013.01)

(58) Field of Classification Search
CPC .......................... A61B 1/0009; A61B 1/2676
See application file for complete search history.

(56) References Cited

U.S. PATENT DOCUMENTS

| | | | | |
|---|---|---|---|---|
| 9,743,073 | B2* | 8/2017 | Huang | ..................... H04N 9/73 |
| 10,614,746 | B2* | 4/2020 | Peng | ..................... G09G 3/2007 |
| 10,659,658 | B2* | 5/2020 | Makino | ..................... H04N 1/60 |
| 2004/0254424 | A1* | 12/2004 | Simkulet | ............. A61B 1/00181 600/176 |
| 2007/0203396 | A1* | 8/2007 | McCutcheon | ..... A61B 1/00147 600/173 |
| 2010/0039507 | A1* | 2/2010 | Imade | ...................... A61B 1/05 348/68 |

(Continued)

*Primary Examiner* — Irfan Habib
(74) *Attorney, Agent, or Firm* — Muncy, Geissler, Olds & Lowe, P.C.

(57) ABSTRACT

A display correction system applied for an endoscope is provided which includes a color checker, a light-shielding tank, an endoscope has a lens that is sleeved in the light shielding tank and the lens is disposed toward the view window, the lens of the light-shielding tank is sequentially aligned the color block of the color checker through the view window to capture the image of the color block. The monitor has a captured image window which is provided for displaying the image of the color that is captured by the endoscope. The display correction device is provided for correcting the image signal from the color block that is transmitted by the endoscope, such that the image is displayed on the monitor is corresponding to the image of the electrical signal, and the color of the image on the monitor is the same as the true color of the color block.

11 Claims, 5 Drawing Sheets

(56) References Cited

U.S. PATENT DOCUMENTS

| | | | |
|---|---|---|---|
| 2010/0091385 A1* | 4/2010 | Togino | G02B 17/004 |
| | | | 359/736 |
| 2011/0230719 A1* | 9/2011 | Katakura | A61B 1/043 |
| | | | 600/156 |
| 2011/0282148 A1* | 11/2011 | Kase | A61B 1/00177 |
| | | | 600/113 |
| 2013/0051642 A1* | 2/2013 | Kanda | G06T 7/90 |
| | | | 382/128 |
| 2015/0065798 A1* | 3/2015 | Kuroda | A61B 1/05 |
| | | | 600/109 |
| 2015/0094537 A1* | 4/2015 | Kuramoto | A61B 1/00057 |
| | | | 600/160 |
| 2015/0109492 A1* | 4/2015 | Hayashi | H01L 27/14605 |
| | | | 348/277 |
| 2015/0181185 A1* | 6/2015 | Ikemoto | A61B 1/0684 |
| | | | 348/71 |
| 2019/0273840 A1* | 9/2019 | Makino | A61B 1/05 |

\* cited by examiner

DISPLAY CORRECTION SYSTEM FOR ENDOSCOPE AND THE CORRECTION METHOD THEREOF

FIELD OF THE INVENTION

The present invention relates to a display technology, particularly relates to a display correction system applied for endoscope and the correction method thereof.

BACKGROUND OF THE INVENTION

In medical diagnosis, the appearance of endoscope is to allow the medical staff to observe the internal organs of the human body through the lens to determine the condition of the internal organs of the human body. The endoscope can be colonoscopy, gastroscopy, and laparoscopic. Even the Da Vinci invasive surgery system also utilizes a mirror that is extended into the inside of the human body and is connected to external display for surgery.

Because the inside of the human body is no light, the lens entering the inside of the human body needs to have the light source to illuminate the internal organs of the human body for observation. Generally, a self-illuminating source is arranged on the lens so that the medical staff can observe it, but because of focusing, white balance and/or light source, the medical staff views the color of the image of the internal organs of the human body is not the same as the true color of that, which may lead to the misjudgment and surgical error by the medical staff.

SUMMARY OF THE INVENTION

According to the disadvantage of the prior art, the major objectives of the present invention is to provide a display correction system applied for an endoscope and the correction method thereof. The major objective is to solve the technical problem is that the displayed image is different from the true color captured by the endoscope due to some factors, for example, focus, white balance and/or light source. The solution to the above technical problem is to capture the image value of the standard color card through the endoscope. After the compensation and the color gamut value calculation of the captured image value, the colors seen from the display is the same as the true color, and conform to the standard specification. The present invention also can utilize the color checker, the display correction device and the endoscope to adjust the compensation values and the parameter values, and the compensation values and the parameter values are stored in the monitor after adjustment, and one or more sets of the compensation values and/or parameter values can be provided for switching by user.

It is another objective of the present invention is to provide a single monitor to correspond to the different kinds of endoscopes to solve the placement space problem of arranging multiple monitors in the clinic. The correction system and the correction method of the present invention can only adjust the color that are captured by the endoscope and is displayed on the monitor. Thus, it is not necessary to adjust the different kinds of monitors and/or different kinds of endoscopes at the same time, so the human effort and the adjustment time can be saved.

It is still an objective of the present invention is to provide a display correction device that can be embedded into the monitor or external to the monitor and the display correction device is connected to the different kinds of monitors.

Therefore, according to above objectives, the present invention provides a display correction system applied for endoscope, which includes a color checker, a light-shielding cartridge, a monitor, and a display correction device. The color checker is composed of 24 different color blocks. The light-shielding bucket is a cylinder shape. A through hole on the first surface of the cylinder shape, a view window on the second surface of the light-shielding bucket, and the through hole is communicated with the view window. The endoscope includes an insertion part and a controlling part, and the insertion part is connected to the controlling part, in which one end of the insertion part has a lens and is sleeved in the through hole of the light-shielding tank and the lens is set toward the view window. One end of the controlling part has an image signal connection terminal, in which the lens set on the light-shielding tank to align each color block of the color checker through the view window sequentially to capture each image of each color block. The monitor includes a captured image window in the center of the screen of the monitor. The captured image window is used to display each image of each color block. The display correction device includes an image calibration module which is provided for calibrating each image of each color block transmitted by the endoscope, in which the image calibration module includes an image input terminal which is provided for receiving each image signal of each image of each color block captured by the lends of the endoscope. A microprocessor of the image calibration module is provided for receiving an electrical signal corresponding to each image signal and performing the calibrating and calculating for the electrical signal. An image output terminal is provided for connecting with the monitor and the electrical signal after calibrating and calculating is outputted on the monitor through the image output terminal, so that the color of each image displayed on the monitor corresponding to each telecommunication signal is the same as the true color of each color block.

DETAILED DESCRIPTION OF THE PREFERRED EMBODIMENT

Figure 1A:
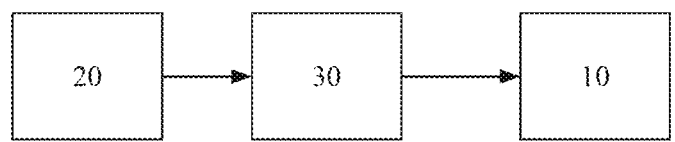
FIG. 1A is a schematic view of showing the external display correction device is connected to monitor and the device capable of outputting image respectively in accordance with the present invention disclosed herein.

First, please refer to FIG. 1A. FIG. 1A is a schematic view of showing the external display correction device is respectively connected to monitor and the device capable of outputting image. In FIG. 1A, the external display correction device 30 (hereinafter refers to display correction device 30) is connected to the device 20 capable of outputting image and the monitor 10 respectively, in which the device 20 capable of outputting image refers to an endoscope captures the observed image and output the observed image. The monitor 10 can be any types of monitor or image device.

In this embodiment, the display correction device 30 is connected to the monitor 10 and the device 20 capable of outputting image by wire. For example, a connection between the display correction device 30 and the device 20 capable of outputting image that can be connected by a communication formats such as a serial digital interface (SDI), a high definition multimedia interface (HDMI), a VGA port or a display port. Therefore, the connection port at one end of the display correction device 30 can be provided with variety of connection terminals for the user to avoid the limitation of the mating between the connection ports and the selection. The above connection method is well-known as the general communication format, and it is not described in detail herein.

In addition, the connection between the display correction device 30 and the monitor 10 can also be used the above connection ports to connect to each other, and the limitation of the mating connection ports and the selection can be avoid, and the use's selectivity in use can be improved.

Figure 1B:
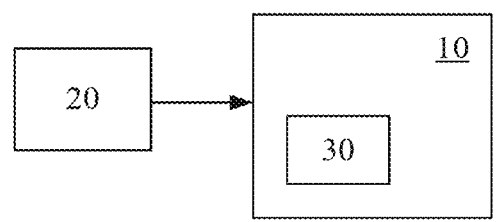
FIG. 1B is a schematic view of showing the endoscope is connected with the monitor includes an embedded display correction device in accordance with another embodiment of the present invention disclosed herein.

Please refer to FIG. 1B. FIG. 1B is a schematic view of showing the endoscope is connected with the monitor and an embedded display correction device. In FIG. 1B, the embedded display correction device 30 is embedded into the monitor 10, and the embedded display correction device 30 is connected to the device 20 capable of outputting image, in which the device 20 capable of outputting image and the monitor 10 are the same as shown in FIG. 1A, and it is not to be described herein. In addition, the detail description of the external display correction device 30 is illustrated as follows, but the function of the external display correction device is the same as the embedded correction device. Moreover, in the embodiment of the present invention, the device 20 capable of outputting image refers specifically to an endoscope can insert inside human body to observe the lesion inside the human body, in which the endoscope can be cystoscopy, gastroscopy, colonoscopy, bronchoscopy, or laparoscopic, but the kinds of the endoscope is not to be limited herein.

Figure 2:
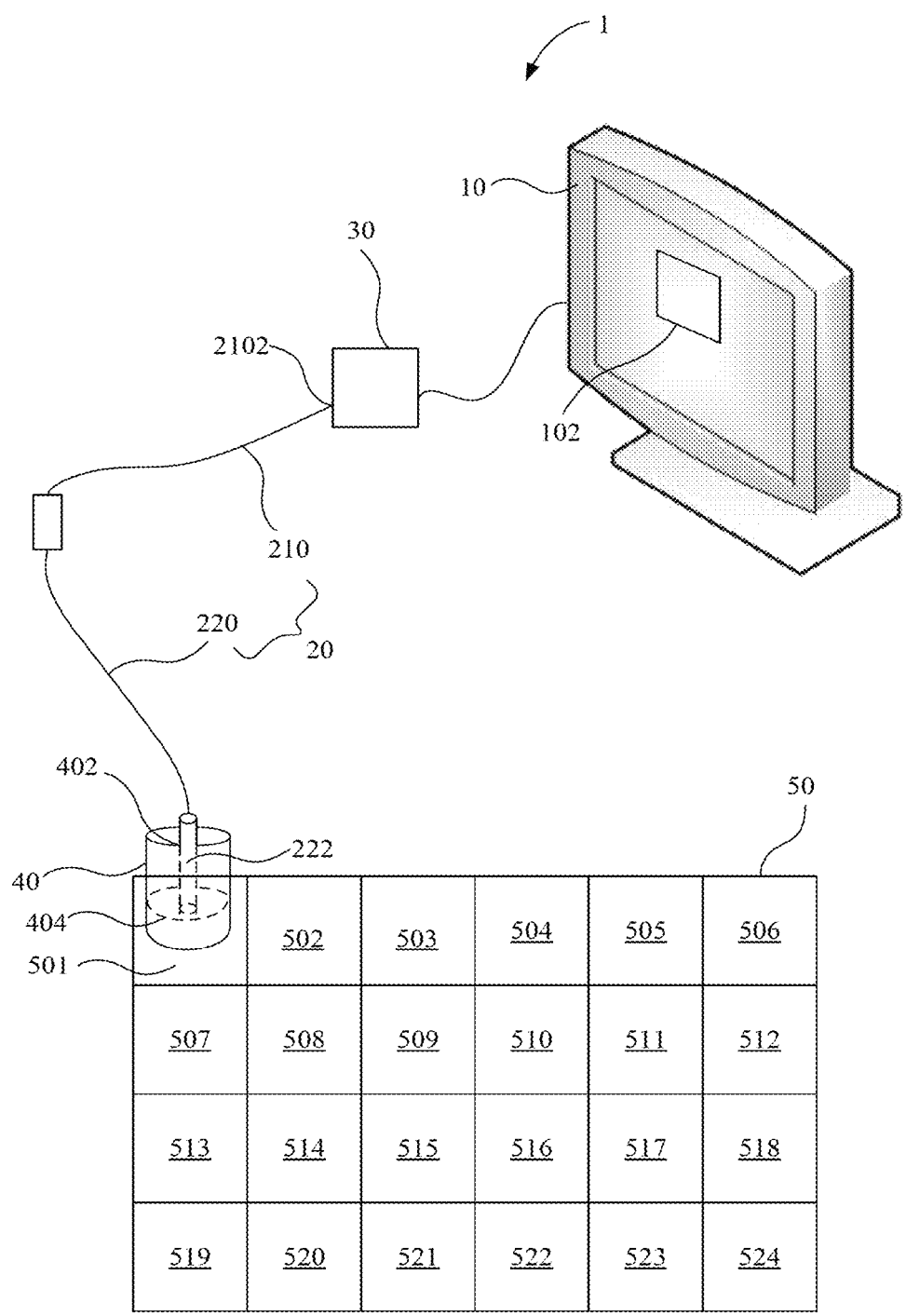
FIG. 2 is a schematic view of showing a display correction system applied for the endoscope in accordance with the present invention disclosed herein.

Next, please refer to FIG. 2. FIG. 2 is a schematic view of showing a display correction system applied for the endoscope. In FIG. 2, the display correction system 1 includes a monitor 10, an endoscope 20, a display correction device 30, a light-shielding tank 40, and a color checker 50, in which the display correction device 30 is respectively connected to the monitor 10 and the endoscope 20. The endoscope 20 is composed of a controlling part 210 and an insertion part 220, in which one end of the controlling part 210 includes an image output terminal 2102 and is connected to the display correction device 30, and one end of the insertion part 220 includes a lens which is provided for viewing and capturing an object (or article) image. In this embodiment, the insertion part 220 with the lens 222 is inserted inside human body (not shown), and the lens 222 is used to observe the lesion inside human body. It should be noted that since there is no light inside human body, the lens 222 of the endoscope 20 inserted into inside human body is used for observing and capturing the image by light source provided by the lens 222 itself. In addition, the detailed structure and the function of the endoscope 20 are not different from the present endoscopes, and the structure and the function of the endoscope are not described herein. Further, the display correction system 1 further includes a light-shielding tank 40 which is a cylinder shape. A through hole 402 is disposed on a first surface of the light-shielding tank 40 and a view window 404 is disposed on a second surface of the light-shielding tank 40. The through hole 402 is communicated with the view window 404. The light-shielding tank 40 is a black light-shielding tank. When the lens 222 of the endoscope 20 is sleeved on the through hole 402 and is disposed toward the view window 404, the endoscope 20 can simulate the lens 222 actually inserted inside human body and has no light source environment, so only the self-illuminating source of the endoscope 20 can illuminate the image to be viewed.

Please continue refer to FIG. 2. The display correction system 1 further includes a color checker 50, in which the color checker 50 is composed of 24 various color blocks. It should be noted that the color checker 50 is a series of 24 natural color, colors, primary colors, and grayscale color block that scientifically formulated in a number of colors. Most of which represent the natural objects such as artificial skin, leaves, and blue sky. Since they represent the color corresponding to the objects and reflect all of the light in the visible spectrum in the same way. Thus, the color blocks can match the color of the natural objects that they represent under any light source, and can also be used in any color reproduction process. The color checker 50 can also be used in digital cameras to create a white balance to ensure the neutral white with accurate and uniform that can be generated under any lighting condition. These color blocks are not only similar in color to their corresponding objects, but also reflect the same light in the visible spectrum. Because of this unique characteristic, each color blocks of the color checker 50 is under any illumination, any color reproduction process that will match the color of its corresponding natural object.

In the present invention, the 24 color blocks 501-524 of the color checker 50 respectively represent a color, a standard red, green and blue color space value (standard Red, Green, Blue, hereinafter referred to as sRGB), and Lab color space are listed in Table 1:

TABLE 1

| No. color | sRGB Value | Lab color space value | | |
|---|---|---|---|---|
| | | L | a | b |
| 501 Dark skin | [115, 82, 68] | 38.0156 | 11.800 | 13.660 |
| 502 Light skin | [194, 150, 130] | 65.666 | 13.677 | 16.891 |
| 503 Blue sky | [98, 122, 157] | 50.628 | 0.376 | −21.607 |
| 504 Foliage | [87, 122, 157] | 43.000 | −15.876 | 20.448 |
| 505 Blue flower | [133, 128, 177] | 55.684 | 12.769 | −25.177 |
| 506 Bluish green | [103, 189, 170] | 71.000 | −30.633 | 1.531 |
| 507 Orange | [214, 126, 44] | 61.133 | 28.108 | 56.132 |
| 508 Purplish blue | [80, 91, 166] | 41.122 | 17.416 | −41.888 |
| 509 Moderate red | [193, 90, 99] | 51.326 | 42.103 | 14.875 |
| 510 Purple | [94, 60, 108] | 31.100 | 24.361 | −22.106 |
| 511 Yellow green | [157, 188, 64] | 71.900 | −28.105 | 57.000 |
| 512 Orange yellow | [224, 163, 46] | 71.036 | 12.604 | 65.000 |
| 513 Blue | [56, 61, 150] | 30.352 | 26.442 | −49.700 |
| 514 Green | [70, 148, 73] | 55.034 | −40.137 | 32.295 |
| 515 Red | [175, 54, 60] | 41.341 | 49.312 | 24.655 |
| 516 Yellow | [231, 199, 31] | 80.703 | −3.664 | 77.551 |
| 517 Magenta | [187, 86, 149] | 51.141 | 48.156 | −15.294 |
| 518 Cyan | [8, 133, 161] | 51.152 | −19.724 | −23.379 |
| 519 White (.0.5) | [243, 243, 242] | 95.818 | −0.171 | 0.470 |
| 520 Neutral 8 (.23) | [200, 200, 200] | 80.604 | 0.00438 | −0.009 |
| 521 Neutral 6.5 (.44) | [160, 160, 160] | 65.868 | 0.0037 | −0.0073 |

TABLE 1-continued

| No. color | sRGB Value | Lab color space value | | |
|---|---|---|---|---|
| | | L | a | b |
| 522 Neutral 5 (.70) | [122, 122, 121] | 51.195 | −0.1968 | 0.540 |
| 523 Neutral 3.5 (.105) | [85, 85, 85] | 36.146 | 0.00236 | −0.0047 |
| 524 Black (1.50) | [52, 52, 52] | 21.704 | 0.0017 | −0.0034 |

In Table 1, the symbol L is a dimension with brightness, symbols a and b represents color-opposing dimensions, so Lab is a CIE XYZ color space coordinate based on nonlinear compression. Thus, the color checker 50 of the present invention is to provide an objective standard to determine the balance between the reproduced color and the true color, and to avoid the difference between the measurement and analysis of the color reproduction during various reproduction processes.

Figure 3:
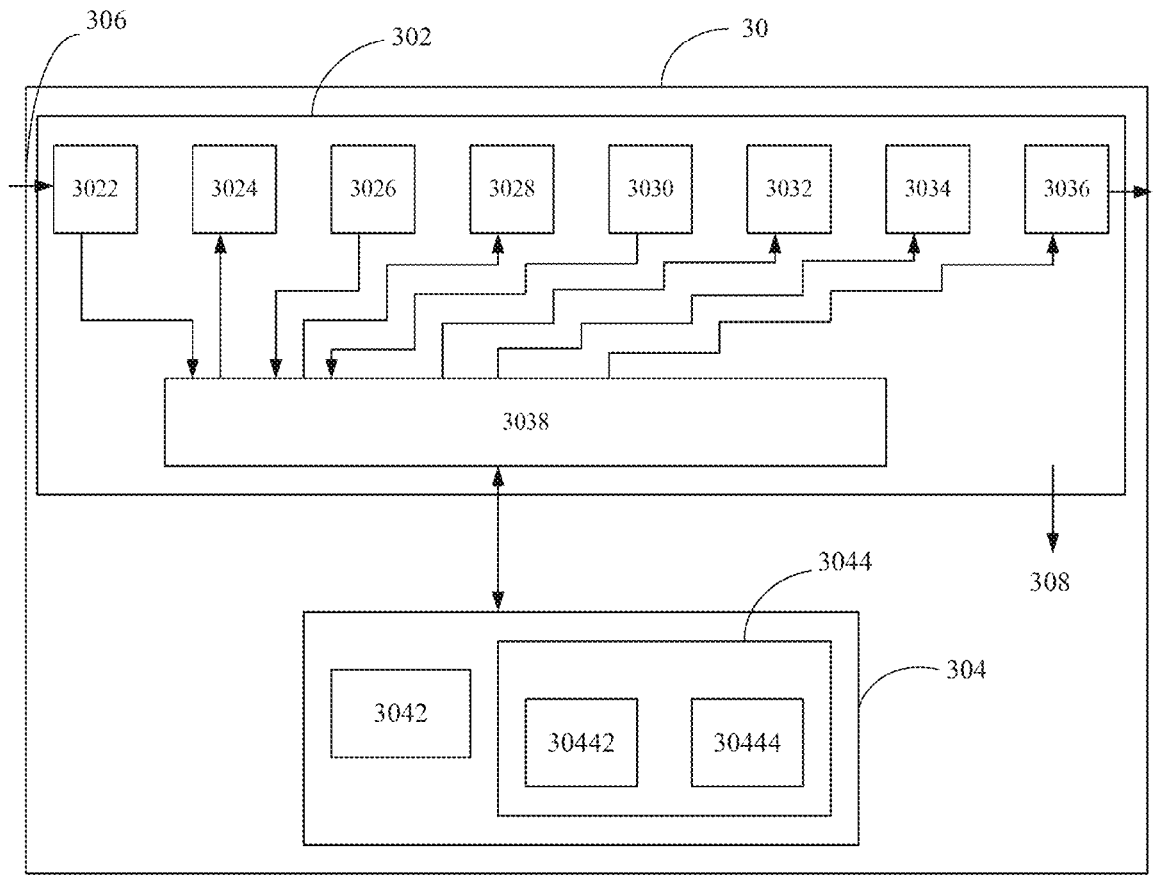
FIG. 3 is a diagram schematic of showing the display correction device in accordance with the present invention disclosed herein.

Next, please refer to FIG. 3. FIG. 3 is a diagram schematic of showing the display correction device. When the embodiment of FIG. 3 is described, it will also be explained together with FIG. 2. In FIG. 3, the display correction device 30 is provided for calibrate the image signal of the object captured by the endoscope 20. The display correction device 30 at least includes an image calibration module 302, a microprocessor 304, an image input terminal 306, and an image output terminal 308. The image calibration module 302 is connected to the image input terminal 306, the microprocessor 304 and the image output terminal 308 respectively. The image input terminal 306 is provided for inputting an image signal of the object which is captured by the lens 222 of the endoscope 20. The image calibration module 302 is provided for receiving the image signal of the object transmitted from the image input terminal 306 and is provided for calibrating the image signal. The microprocessor 304 is provided for receiving the electrical signal which is detected by the optical sensor (not shown) measures the monitor 10, Then, the electrical signal is outputted to the monitor 10 through the image output module 304 after calibration and the operation processes, and the image which is captured by the endoscope 20 and is calibrated by the display correction device 30 will be displayed by the monitor. Such image is to be provided for diagnosing by the user, such as medical staff. It should be noted that the optical sensor may be embedded into the display correction device 30 or embedded into the monitor 10.

As shown in FIG. 3, the image calibration module 302 includes a color checker original data catch module 3022, a first 3×3 color mapping_1 matrix module 3024, a first color checker adjusted data catch_1 module 3026, a second 3×3 color mapping_2 matrix module 3028, a second color checker adjusted data catch_2 module 3030, sRGB Gamma 2.2 calibration module 3032, a 3×3 gamut mapping matrix module 3034, the De-gamma calibration module 3036 and flex bus 3038. The following illustrates the function of each module.

Color checker original data catch module 3022: The original image is to be captured that is placed in the captured image window 102 at the center screen of the monitor 10 by the image calibration module 302 for capturing the RGB value of 16 pixels of the image in the captured image window 102. Then, the average value of RGB value of 16 pixels is calculated. In this embodiment of the present invention, during the capturing image process of the color checker 50, the capturing process will sequentially capture each image of each color block from color block 501 to color block 524 to obtain each RGB value of 24 colors, in which R (red) value, G (green) value, and B (blue) value of each color blocks 501-524 is 8 bits, so that there are 24 RGB values are transmitted to the microprocessor 304 through the flex bus 3038.

First 3×3 color mapping_1 matrix module 3024: the first 3×3 color mapping_1 matrix module 3024 is provided for receiving the coefficient values calculated by the microprocessor 304, in which the coefficient value is required for the operation of the first 3×3 color mapping_1 matrix Then, these coefficient values will be transmitted to the image calibration module 302 for 3×3 matrix operation processing.

The coefficient values of 3×3 color mapping_1 matrix is expressed as $[AR_x, AG_x, AB_x]$, Equation (1), the coefficient values is RGB obtained by the color checker original data catch module 3022 to capture the 24 color blocks 501-524 of the color checker 50, and the coefficient values can be expressed respectively by the following Equation (2)-Equation (25).

$$[AR_1, AG_1, AB_1], \quad \text{Equation (2);}$$

$$[AR_2, AG_2, AB_2], \quad \text{Equation (3);}$$

$$[AR_3, AG_3, AB_3], \quad \text{Equation (4);}$$

$$[AR_4, AG_4, AB_4], \quad \text{Equation (5);}$$

$$[AR_5, AG_5, AB_5], \quad \text{Equation (6);}$$

$$[AR_6, AG_6, AB_6], \quad \text{Equation (7);}$$

$$[AR_8, AG_8, AB_8], \quad \text{Equation (8);}$$

$$[AR_8, AG_8, AB_8], \quad \text{Equation (9);}$$

$$[AR_9, AG_9, AB_9], \quad \text{Equation (10);}$$

$$[AR_{10}, AG_{10}, AB_{10}], \quad \text{Equation (11);}$$

$$[AR_{11}, AG_{11}, AB_{11}], \quad \text{Equation (12);}$$

$$[AR_{12}, AG_{12}, AB_{12}], \quad \text{Equation (13);}$$

$$[AR_{13}, AG_{13}, AB_{13}], \quad \text{Equation (14);}$$

$$[AR_{14}, AG_{14}, AB_{14}], \quad \text{Equation (15);}$$

$$[AR_{15}, AG_{15}, AB_{15}], \quad \text{Equation (16);}$$

$$[AR_{16}, AG_{16}, AB_{16}], \quad \text{Equation (17);}$$

$$[AR_{17}, AG_{17}, AB_{17}], \quad \text{Equation (18);}$$

$$[AR_{18}, AG_{18}, AB_{18}], \quad \text{Equation (19);}$$

$$[AR_{19}, AG_{19}, AB_{19}], \quad \text{Equation (20);}$$

$$[AR_{20}, AG_{20}, AB_{20}], \quad \text{Equation (21);}$$

$$[AR_{21}, AG_{21}, AB_{21}], \quad \text{Equation (22);}$$

$$[AR_{22}, AG_{22}, AB_{22}], \quad \text{Equation (23);}$$

$$[AR_{23}, AG_{23}, AB_{23}], \quad \text{Equation (24); and}$$

$$[AR_{24}, AG_{24}, AB_{24}], \quad \text{Equation(25),}$$

where x of $[AR_x, AG_x, AB_x]$ in Equation (1) is 1 to 24, which indicates each color blocks 501-524 of the color checker 50.

Thus, equation (2) to equation (25) respectively represent the original RGB value of each color blocks 501-524 of the color checker 50 is to be captured by the endoscope 20, therefore, $[AR_1, AG_1, AB_1]$, Equation (2) represents the original RGB values of the color block 501 of dark skin captured by the endoscope 20 to be calibrated;

$[AR_2, AG_2, AB_2]$, Equation (3) represents the original RGB values of the color block 502 of light skin captured by the endoscope 20 to be calibrated;

$[AR_3, AG_3, AB_3]$, Equation (4) represents the original RGB values of the color block 503 of blue sky captured by the endoscope 20 to be calibrated;

$[AR_4, AG_4, AB_4]$, Equation (5) represents the original RGB values of the color block 504 of foliage color captured by the endoscope 20 to be calibrated;

$[AR_5, AG_5, AB_5]$, Equation (6) represents the original RGB values of the color block 505 of blue flower color captured by the endoscope 20 to be calibrated;

$[AR_6, AG_6, AB_6]$, Equation (7) represents the original RGB values of the color block 506 of bluish green color captured by the endoscope 20 to be calibrated;

$[AR_7, AG_7, AB_7]$, Equation (8) represents the original RGB values of the color block 507 of orange color captured by the endoscope 20 to be calibrated;

$[AR_8, AG_8, AB_8]$, Equation (9) represents the original RGB values of the color block 508 of purplish blue color captured by the endoscope 20 to be calibrated;

$[AR_9, AG_9, AB_9]$, Equation (10) represents the original RGB values of the color block 509 of moderate red color captured by the endoscope 20 to be calibrated;

$[AR_{10}, AG_{10}, AB_{10}]$, Equation (11) represents the original RGB values of the color block 510 of purple color captured by the endoscope 20 to be calibrated;

$[AR_{11}, AG_{11}, AB_{11}]$, Equation (12) represents the original RGB values of the color block 511 of yellow green color captured by the endoscope 20 to be calibrated;

$[AR_{12}, AG_{12}, AB_{12}]$, Equation (13) represents the original RGB values of the color block 512 of orange yellow color captured by the endoscope 20 to be calibrated;

$[AR_{13}, AG_{13}, AB_{13}]$, Equation (14) represents the original RGB values of the color block 513 of blue color captured by the endoscope 20 to be calibrated;

$[AR_{14}, AG_{14}, AB_{14}]$, Equation (15) represents the original RGB values of the color block 514 of green color captured by the endoscope 20 to be calibrated;

$[AR_{15}, AG_{15}, AB_{15}]$, Equation (16) represents the original RGB values of the color block 515 of red color captured by the endoscope 20 to be calibrated;

$[AR_{16}, AG_{16}, AB_{16}]$, Equation (17) represents the original RGB values of the color block 516 of yellow color captured by the endoscope 20 to be calibrated;

$[AR_{17}, AG_{17}, AB_{17}]$, Equation (18) represents the original RGB values of the color block 517 of magenta color captured by the endoscope 20 to be calibrated;

$[AR_{18}, AG_{18}, AB_{18}]$, Equation (19) represents the original RGB values of the color block 518 of cyan color captured by the endoscope 20 to be calibrated;

$[AR_{19}, AG_{19}, AB_{19}]$, Equation (20) represents the original RGB values of the color block 519 of white (0.5) color captured by the endoscope 20 to be calibrated;

$[AR_{20}, AG_{20}, AB_{20}]$, Equation (21) represents the original RGB values of the color block 520 of neutral 8 (0.23) color captured by the endoscope 20 to be calibrated;

$[AR_{21}, AG_{21}, AB_{21}]$, Equation (22) represents the original RGB values of the color block 521 of neutral 6.5 (0.44) color captured by the endoscope 20 to be calibrated;

$[AR_{22}, AG_{22}, AB_{22}]$, Equation (23) represents the original RGB values of the color block 522 of neutral 5 (0.70) color captured by the endoscope 20 to be calibrated;

$[AR_{23}, AG_{23}, AB_{23}]$, Equation (24) represents the original RGB values of the color block 523 of Neutral 3.5 (0.105) color captured by the endoscope 20 to be calibrated; and $[AR_{24}, AG_{24}, AB_{24}]$, Equation (25) represents the original RGB values of the color block 524 of black (1.50) color captured by the endoscope 20 to be calibrated.

Next, the RGB value of 24 color blocks 501-524 of the color checker 50 are converted from 24×3 matrix to A transposed matrix, as represented by equation (26) and equation (27):

$$A_{24\times 3} = \begin{bmatrix} AR_1 & AG_1 & AB_1 \\ \ldots & \ldots & \ldots \\ AR_{24} & AG_{24} & AB_{24} \end{bmatrix} \quad \text{Equation (26)}$$

$$A_{24\times 3}^T = \begin{bmatrix} AR_1 & \ldots & AR_{24} \\ AG_1 & \ldots & AG_{24} \\ AB_1 & \ldots & AB_{24} \end{bmatrix} \quad \text{Equation (27)}$$

The equation (26) ($A_{24\times 3}$) and equation (27) ($A_{24\times 3}^T$) are multiplied to obtain a B matrix of equation (28):

$$B_{24\times 3} = A_{24\times 3} \times A_{24\times 3}^T = \begin{bmatrix} AR_1 & AG_1 & AB_1 \\ \ldots & \ldots & \ldots \\ AR_{24} & AG_{24} & AB_{24} \end{bmatrix} \times$$

$$\begin{bmatrix} AR_1 & \ldots & AR_{24} \\ AG_1 & \ldots & AG_{24} \\ AB_1 & \ldots & AB_{24} \end{bmatrix} = \begin{bmatrix} B_{11} & B_{12} & B_{13} \\ B_{21} & B_{22} & B_{23} \\ B_{31} & B_{32} & B_{33} \end{bmatrix} \quad \text{Equation (28)}$$

The B matrix ($B_{24\times 3}$) (equation (28)) is calculated to obtain the inverse matrix $B_{24\times 3}^{-1}$, $$B_{24\times 3}^{-1} = \begin{bmatrix} \begin{vmatrix} B_{22} & B_{23} \\ B_{32} & B_{33} \end{vmatrix} & \begin{vmatrix} B_{13} & B_{12} \\ B_{33} & B_{32} \end{vmatrix} & \begin{vmatrix} B_{12} & B_{13} \\ B_{22} & B_{23} \end{vmatrix} \\ \begin{vmatrix} B_{23} & B_{21} \\ B_{33} & B_{31} \end{vmatrix} & \begin{vmatrix} B_{11} & B_{13} \\ B_{31} & B_{33} \end{vmatrix} & \begin{vmatrix} B_{13} & B_{11} \\ B_{23} & B_{21} \end{vmatrix} \\ \begin{vmatrix} B_{21} & B_{22} \\ B_{31} & B_{32} \end{vmatrix} & \begin{vmatrix} B_{12} & B_{11} \\ B_{32} & B_{31} \end{vmatrix} & \begin{vmatrix} B_{11} & B_{12} \\ B_{21} & B_{22} \end{vmatrix} \end{bmatrix} \quad \text{Equation (29)}$$

Then, the transposed matrix of equation (27) and the 24×3 matrix ($S_{24\times 3}$) of the standard RGB values of the color checker 50 to obtain matrix $C_{24\times 3}$ wherein $S_{24\times 3}$ matrix can be expressed as $$\begin{bmatrix} SR_1 & SG_1 & SB_1 \\ \ldots & \ldots & \ldots \\ SR_{24} & SG_{24} & SB_{24} \end{bmatrix}. \quad \text{Equation (30)}$$

Accordingly, the matrix $C_{24\times 3}$ is expressed by Equation (31):

$$C_{24\times 3} = A_{24\times 3}^T \times S_{24\times 3} = \begin{bmatrix} AR_1 & \ldots & AR_{24} \\ AG_1 & \ldots & AG_{24} \\ AB_1 & \ldots & AB_{24} \end{bmatrix} \times \quad \text{Equation (31)}$$

-continued $$\begin{bmatrix} SR_1 & SG_1 & SB_1 \\ \ldots & \ldots & \ldots \\ SR_{24} & SG_{24} & SB_{24} \end{bmatrix} = \begin{bmatrix} AR_1 & \ldots & AR_{24} \\ AG_1 & \ldots & AG_{24} \\ AB_1 & \ldots & AB_{24} \end{bmatrix} \times$$

$$\begin{bmatrix} 115 & 82 & 68 \\ 194 & 150 & 130 \\ 98 & 122 & 157 \\ 87 & 108 & 67 \\ 133 & 128 & 177 \\ 103 & 189 & 170 \\ 214 & 126 & 44 \\ 80 & 91 & 166 \\ 193 & 90 & 99 \\ 94 & 60 & 108 \\ 157 & 188 & 64 \\ 224 & 163 & 46 \\ 56 & 61 & 150 \\ 70 & 148 & 73 \\ 175 & 54 & 60 \\ 231 & 199 & 31 \\ 187 & 86 & 149 \\ 8 & 133 & 161 \\ 243 & 243 & 242 \\ 200 & 200 & 200 \\ 160 & 160 & 160 \\ 122 & 122 & 121 \\ 85 & 85 & 85 \\ 52 & 52 & 52 \end{bmatrix} = \begin{bmatrix} C_{11} & C_{12} & C_{13} \\ C_{21} & C_{22} & C_{23} \\ C_{31} & C_{32} & C_{33} \end{bmatrix}$$

The equation (29) ($B_{24\times3}^{-1}$ inverse matrix) and equation (31) ($C_{24\times3}$) are multiplied to obtain $D_{3\times3}$ matrix:

$$D_{3\times3} = \quad\text{Equation (32)}$$

$$B_{24\times3}^{-1} \times C_{24\times3} = \begin{bmatrix} \begin{vmatrix} B_{22} & B_{23} \\ B_{32} & B_{33} \end{vmatrix} & \begin{vmatrix} B_{13} & B_{12} \\ B_{33} & B_{32} \end{vmatrix} & \begin{vmatrix} B_{12} & B_{13} \\ B_{22} & B_{23} \end{vmatrix} \\ \begin{vmatrix} B_{23} & B_{21} \\ B_{33} & B_{31} \end{vmatrix} & \begin{vmatrix} B_{11} & B_{13} \\ B_{31} & B_{33} \end{vmatrix} & \begin{vmatrix} B_{13} & B_{11} \\ B_{23} & B_{21} \end{vmatrix} \\ \begin{vmatrix} B_{21} & B_{22} \\ B_{31} & B_{32} \end{vmatrix} & \begin{vmatrix} B_{12} & B_{11} \\ B_{32} & B_{31} \end{vmatrix} & \begin{vmatrix} B_{11} & B_{12} \\ B_{21} & B_{22} \end{vmatrix} \end{bmatrix} \times$$

$$\begin{bmatrix} C_{11} & C_{12} & C_{13} \\ C_{21} & C_{22} & C_{23} \\ C_{31} & C_{32} & C_{33} \end{bmatrix} = \begin{bmatrix} D_{11} & D_{11} & D_{13} \\ D_{21} & D_{22} & D_{23} \\ D_{31} & D_{23} & D_{33} \end{bmatrix}$$

$D_{3\times3}$ matrix is transposed to obtain $D_{3\times3}^T$ matrix, $D_{3\times3}^T =$ $$\begin{bmatrix} D_{11} & D_{21} & D_{31} \\ D_{12} & D_{22} & D_{32} \\ D_{13} & D_{23} & D_{33} \end{bmatrix}, \quad\text{Equation (33)}$$

and let $E_{3\times3}$ matrix be equal to the $D_{3\times3}^T$ transposed matrix:

$$E_{3\times3} = D_{3\times3}^T = \begin{bmatrix} E_{11} & E_{11} & E_{13} \\ E_{21} & E_{22} & E_{23} \\ E_{31} & E_{23} & E_{33} \end{bmatrix} \quad\text{Equation (33-1)}$$

Therefore, the RGB value ($O'_{RGB}$) of the output image is the product of E matrix and the RGB value ($I_{RGB}$) of the input image, and the mathematical expression is expressed by equation (34):

$$O'_{RGB} = E_{3\times3} \times I_{RGB} = \begin{bmatrix} R' \\ G' \\ B' \end{bmatrix} = \begin{bmatrix} E_{11} & E_{12} & E_{13} \\ E_{21} & E_{22} & E_{23} \\ E_{31} & E_{32} & E_{33} \end{bmatrix} \times \begin{bmatrix} R \\ G \\ B \end{bmatrix} \quad\text{Equation (34)}$$

Therefore, the R, G, B values of the output image are expressed by Equation (35)~Equation (37):

$$R' = E_{11}R + E_{12}G + E_{13}B \quad\text{Equation (35);}$$

$$G' = E_{21}R + E_{22}G + E_{23}B \quad\text{Equation (36); and}$$

$$B' = E_{31}R + E_{32}G + E_{33}B \quad\text{Equation (37),}$$

where $E_{11}$–$E_{33}$ are 9 coefficient values that required for the operation of the first 3×3 color mapping_1 matrix.

First color checker adjusted data catch_1 module 3026: the image value processed by the color checker original data catch module 3024 is placed in the captured image window 102 of the monitor 10, and the first color checker adjusted data catch_1 module 3026 is used to capture the RGB value of 16 pixels within the captured image window 102, and the RGB value of 16 pixels are calculated to obtain the RGB average values of 16 pixels. Finally, the values of the captured image RGB is obtained. Accordingly, in the present invention, the RGB values of 24 color blocks 501-524 are obtained in the capturing image process by the color checker 50, and the RGB value of 24 color blocks 501-524 are transmitted to the microprocessor 304.

Second 3×3 color mapping_2 matrix module 3028: the coefficient value corresponding to the transposed matrix corresponding to the second 3×3 color mapping_2 matrix is calculated by the microprocessor 304, and the coefficient values are transmitted to the image calibration module 302 to perform a 3×3 matrix operation processing.

The coefficient values of second 3×3 color mapping_2 matrix are expressed by equation (38): $[A'R'_x, A'G'_x, A'B'_x]$ Equation (38). The coefficient value is the image of each color blocks 501-524 of the color blocks 50 captured by the endoscope 20 and is converted by the first 3×3 color mapping_1 matrix module 3024. Then, the coefficient value is further operated by the second color checker adjusted data catch_2 module 3030, the coefficient values is expressed by equation (39)-equation (62):

$$[A'R'_1, A'G'_1, AB'_1] \quad\text{Equation (39);}$$

$$[A'R'_2, A'G'_2, A'B'_2] \quad\text{Equation (40);}$$

$$[A'R'_3, A'G'_3, AB'_3] \quad\text{Equation (41);}$$

$$[A'R'_4, A'G'_4, A'B'_4] \quad\text{Equation (42);}$$

$$[A'R'_5, A'G'_5, A'B'_5] \quad\text{Equation (43);}$$

$$[A'R'_6, A'G'_6, A'B'_6] \quad\text{Equation (44);}$$

$$[A'R'_7, A'G'_7, A'B'_7] \quad\text{Equation (45);}$$

$$[A'R'_8, A'G'_8, A'B'_8] \quad \text{Equation (46)};$$

$$[A'R'_9, A'G'_9, A'B'_9] \quad \text{Equation (47)};$$

$$[A'R'_{10}, A'G'_{10}, A'B'_{10}] \quad \text{Equation (48)};$$

$$[A'R'_{11}, A'G'_{11}, A'B'_{11}] \quad \text{Equation (49)};$$

$$[A'R'_{12}, A'G'_{12}, A'B'_{12}] \quad \text{Equation (50)};$$

$$[A'R'_{13}, A'G'_{13}, A'B'_{13}] \quad \text{Equation (51)};$$

$$[A'R'_{14}, A'G'_{14}, A'B'_{14}] \quad \text{Equation (52)};$$

$$[A'R'_{15}, A'G'_{15}, A'B'_{15}] \quad \text{Equation (53)};$$

$$[A'R'_{16}, A'G'_{16}, A'B'_{16}] \quad \text{Equation (54)};$$

$$[A'R'_{17}, A'G'_{17}, A'B'_{17}] \quad \text{Equation (55)};$$

$$[A'R'_{18}, A'G'_{18}, A'B'_{18}] \quad \text{Equation (56)};$$

$$[A'R'_{19}, A'G'_{19}, A'B'_{19}] \quad \text{Equation (57)};$$

$$[A'R'_{20}, A'G'_{20}, A'B'_{20}] \quad \text{Equation (58)};$$

$$[A'R'_{21}, A'G'_{21}, A'B'_{21}] \quad \text{Equation (59)};$$

$$[A'R'_{22}, A'G'_{22}, A'B'_{22}] \quad \text{Equation (60)};$$

$$[A'R'_{23}, A'G'_{23}, A'B'_{23}] \quad \text{Equation (61); and}$$

$$[A'R'_{24}, A'G'_{24}, A'B'_{24}] \quad \text{Equation (62), where,}$$

$[A'R'_1, A'G'_1, A'B'_1]$ Equation (39) represented the RGB value of the color block 501 (dark skin color) is captured by the endoscope 20 and operated by first 3×3 color mapping_1 matrix operation;

$[A'R'_2, A'G'_2, A'B'_2]$ Equation (40) represented the RGB value of the color block 502 (light skin color) is captured by the endoscope 20 and operated by first 3×3 color mapping_1 matrix operation;

$[A'R'_3, A'G'_3, A'B'_3]$ Equation (41) represented the RGB value of the color block 503 (blue sky color) is captured by the endoscope 20 and operated by first 3×3 color mapping_1 matrix operation;

$[A'R'_4, A'G'_4, A'B'_4]$ Equation (42) represented the RGB value of the color block 504 (foliage color) is captured by the endoscope 20 and operated by first 3×3 color mapping_1 matrix operation;

$[A'R'_5, A'G'_5, A'B'_5]$ Equation (43) represented the RGB value of the color block 505 (blue flower color) is captured by the endoscope 20 and operated by first 3×3 color mapping_1 matrix operation;

$[A'R'_6, A'G'_6, A'B'_6]$ Equation (44) represented the RGB value of the color block 506 (bluish green color) is captured by the endoscope 20 and operated by first 3×3 color mapping_1 matrix operation;

$[A'R'_7, A'G'_7, A'B'_7]$ Equation (45) represented the RGB value of the color block 507 (orange color) is captured by the endoscope 20 and operated by first 3×3 color mapping_1 matrix operation;

$[A'R'_8, A'G'_8, A'B'_8]$ Equation (46) represented the RGB value of the color block 508 (purplish blue color) is captured by the endoscope 20 and operated by first 3×3 color mapping_1 matrix operation;

$[A'R'_9, A'G'_9, A'B'_9]$ Equation (47) represented the RGB value of the color block 509 (moderate red color) is captured by the endoscope 20 and operated by first 3×3 color mapping_1 matrix operation;

$[A'R'_{10}, A'G'_{10}, A'B'_{10}]$ Equation (48) represented the RGB value of the color block 510 (purple color) is captured by the endoscope 20 and operated by first 3×3 color mapping_1 matrix operation;

$[A'R'_{11}, A'G'_{11}, A'B'_{11}]$ Equation (49) represented the RGB value of the color block 511 (yellow green color) is captured by the endoscope 20 and operated by first 3×3 color mapping_1 matrix operation;

$[A'R'_{12}, A'G'_{12}, A'B'_{12}]$ Equation (50) represented the RGB value of the color block 512 (orange yellow color) is captured by the endoscope 20 and operated by first 3×3 color mapping_1 matrix operation;

$[A'R'_{13}, A'G'_{13}, A'B'_{13}]$ Equation (51) represented the RGB value of the color block 513 (blue color) is captured by the endoscope 20 and operated by first 3×3 color mapping_1 matrix operation;

$[A'R'_{14}, A'G'_{14}, A'B'_{14}]$ Equation (52) represented the RGB value of the color block 514 (green color) is captured by the endoscope 20 and operated by first 3×3 color mapping_1 matrix operation;

$[A'R'_{15}, A'G'_{15}, A'B'_{15}]$ Equation (53) represented the RGB value of the color block 515 (red color) is captured by the endoscope 20 and operated by first 3×3 color mapping_1 matrix operation;

$[A'R'_{16}, A'G'_{16}, A'B'_{16}]$ Equation (54) represented the RGB value of the color block 516 (yellow color) is captured by the endoscope 20 and operated by first 3×3 color mapping_1 matrix operation;

$[A'R'_{17}, A'G'_{17}, A'B'_{17}]$ Equation (55) represented the RGB value of the color block 517 (magenta color) is captured by the endoscope 20 and operated by first 3×3 color mapping_1 matrix operation;

$[A'R'_{18}, A'G'_{18}, A'B'_{18}]$ Equation (56) represented the RGB value of the color block 518 (cyan color) is captured by the endoscope 20 and operated by first 3×3 color mapping_1 matrix operation;

$[A'R'_{19}, A'G'_{19}, A'B'_{19}]$ Equation (57) represented the RGB value of the color block 519 (white color) is captured by the endoscope 20 and operated by first 3×3 color mapping_1 matrix operation;

$[A'R'_{20}, A'G'_{20}, A'B'_{20}]$ Equation (58) represented the RGB value of the color block 520 (Neutral 8 color) is captured by the endoscope 20 and operated by first 3×3 color mapping_1 matrix operation;

$[A'R'_{21}, A'G'_{21}, A'B'_{21}]$ Equation (59) represented the RGB value of the color block 521 (Neutral 6.5 color) is captured by the endoscope 20 and operated by first 3×3 color mapping_1 matrix operation;

$[A'R'_{22}, A'G'_{22}, A'B'_{22}]$ Equation (60) represented the RGB value of the color block 522 (Neutral 5 color) is captured by the endoscope 20 and operated by first 3×3 color mapping_1 matrix operation;

$[A'R'_{23}, A'G'_{23}, A'B'_{23}]$ Equation (61) represented the RGB value of the color block 523 (Neutral 3.5 color) is captured by the endoscope 20 and operated by first 3×3 color mapping_1 matrix operation; and $[A'R'_{24}, A'G'_{24}, A'B'_{24}]$ Equation (62) represented the RGB value of the color block 524 (block color) is captured by the endoscope 20 and operated by first 3×3 color mapping_1 matrix operation.

Similarly, the R'、G'、B' values of above 24 color blocks 501-524 are converted from $A'_{24\times23}$ matrix to $A'^T$ transposed matrix, $A'_{24\times23}$ matrix and $A'^T$ transposed matrix are expressed respectively by equation (63) and equation (64):

$$A'_{24\times 3} = \begin{bmatrix} A'R'_1 & A'G'_1 & A'B'_1 \\ \ldots & \ldots & \ldots \\ A'R'_{24} & A'G'_{24} & A'B'_{24} \end{bmatrix}, \quad \text{Equation (63)}$$

$$A'^T_{24\times 3} = \begin{bmatrix} A'R'_1 & \ldots & A'R'_{24} \\ A'G'_1 & \ldots & A'G'_{24} \\ A'B'_1 & \ldots & A'B'_{24} \end{bmatrix}. \quad \text{Equation (64)}$$

Next, the $A'_{24\times 23}$ and $A'_{24\times 23}{}^T$ are multiplied to obtain $B'_{24\times 3}$ matrix as expressed by equation (65):

$$B'_{24\times 3} = A'_{24\times 3} = A'^T_{24\times 3} = \begin{bmatrix} A'R'_1 & A'G'_1 & A'B'_1 \\ \ldots & \ldots & \ldots \\ A'R'_{24} & A'G'_{24} & A'B'_{24} \end{bmatrix} \times \quad \text{Equation (65)}$$

$$\begin{bmatrix} A'R'_1 & \ldots & A'R'_{24} \\ A'G'_1 & \ldots & A'G'_{24} \\ A'B'_1 & \ldots & A'B'_{24} \end{bmatrix} = \begin{bmatrix} B'_{11} & B'_{12} & B'_{13} \\ B'_{21} & B'_{22} & B'_{23} \\ B'_{31} & B'_{32} & B'_{33} \end{bmatrix}.$$

The $B'_{24\times 3}$ matrix is calculated to obtain the inverse matrix $B_{24\times 3}{}^{-1}$ as expressed by equation (66):

$$B'^{-1}_{24\times 3} = \begin{bmatrix} \begin{vmatrix} B'_{22} & B'_{23} \\ B'_{32} & B'_{33} \end{vmatrix} & \begin{vmatrix} B'_{13} & B'_{12} \\ B'_{33} & B'_{32} \end{vmatrix} & \begin{vmatrix} B'_{12} & B'_{13} \\ B'_{22} & B'_{23} \end{vmatrix} \\ \begin{vmatrix} B'_{23} & B'_{21} \\ B'_{33} & B'_{31} \end{vmatrix} & \begin{vmatrix} B'_{11} & B'_{13} \\ B'_{31} & B'_{33} \end{vmatrix} & \begin{vmatrix} B'_{13} & B'_{11} \\ B'_{23} & B'_{21} \end{vmatrix} \\ \begin{vmatrix} B'_{21} & B'_{22} \\ B'_{31} & B'_{32} \end{vmatrix} & \begin{vmatrix} B'_{12} & B'_{11} \\ B'_{32} & B'_{31} \end{vmatrix} & \begin{vmatrix} B'_{11} & B'_{12} \\ B'_{21} & B'_{22} \end{vmatrix} \end{bmatrix} \quad \text{Equation (66)}$$

$A'_{24\times 3}$ transposed matrix and $S_{24\times 3}$ matrix of the standard RGB values of the color checker 50 to obtain $C'_{3\times 3}$ matrix, wherein $S_{24\times 3}$ is the same as the above equation (30), $$S_{24\times 3} = \begin{bmatrix} SR_1 & SG_1 & SB_1 \\ \ldots & \ldots & \ldots \\ SR_{24} & SG_{24} & SB_{24} \end{bmatrix},$$

so that $C'_{3\times 3}$ matrix is expressed by equation (67):

$$C'_{3\times 3} = A'^T_{24\times 3} \times S_{24\times 3} = \quad \text{Equation (67)}$$

$$\begin{bmatrix} A'R'_1 & \ldots & A'R'_{24} \\ A'G'_1 & \ldots & A'G'_{24} \\ A'B'_1 & \ldots & A'B'_{24} \end{bmatrix} \times \begin{bmatrix} SR_1 & SG_1 & SB_1 \\ \ldots & \ldots & \ldots \\ SR_{24} & SG_{24} & SB_{24} \end{bmatrix} =$$

$$\begin{bmatrix} A'R'_1 & \ldots & A'R'_{24} \\ A'G'_1 & \ldots & A'G'_{24} \\ A'B'_1 & \ldots & A'B'_{24} \end{bmatrix} \times \begin{bmatrix} 115 & 82 & 68 \\ 194 & 150 & 130 \\ 98 & 122 & 157 \\ 87 & 108 & 67 \\ 133 & 128 & 177 \\ 103 & 189 & 170 \\ 214 & 126 & 44 \\ 80 & 91 & 166 \\ 193 & 90 & 99 \\ 94 & 60 & 108 \\ 157 & 188 & 64 \\ 224 & 163 & 46 \\ 56 & 61 & 150 \\ 70 & 148 & 73 \\ 175 & 54 & 60 \\ 231 & 199 & 31 \\ 187 & 86 & 149 \\ 8 & 133 & 161 \\ 243 & 243 & 242 \\ 200 & 200 & 200 \\ 160 & 160 & 160 \\ 122 & 122 & 121 \\ 85 & 85 & 85 \\ 52 & 52 & 52 \end{bmatrix} =$$

$$\begin{bmatrix} C'_{11} & C'_{12} & C'_{13} \\ C'_{21} & C'_{22} & C'_{23} \\ C'_{31} & C'_{32} & C'_{33} \end{bmatrix}.$$

Next, $B'_{24\times 3}{}^{-1}$ matrix and $C'_{3\times 3}$ matrix are multiplied to obtain $D'_{3\times 3}$ matrix is expressed by equation (68):

$$D'_{3\times 3} = \begin{bmatrix} \begin{vmatrix} B'_{22} & B'_{23} \\ B'_{32} & B'_{33} \end{vmatrix} & \begin{vmatrix} B'_{13} & B'_{12} \\ B'_{33} & B'_{32} \end{vmatrix} & \begin{vmatrix} B'_{12} & B'_{13} \\ B'_{22} & B'_{23} \end{vmatrix} \\ \begin{vmatrix} B'_{23} & B'_{21} \\ B'_{33} & B'_{31} \end{vmatrix} & \begin{vmatrix} B'_{11} & B'_{13} \\ B'_{31} & B'_{33} \end{vmatrix} & \begin{vmatrix} B'_{13} & B'_{11} \\ B'_{23} & B'_{21} \end{vmatrix} \\ \begin{vmatrix} B'_{21} & B'_{22} \\ B'_{31} & B'_{32} \end{vmatrix} & \begin{vmatrix} B'_{12} & B'_{11} \\ B'_{32} & B'_{31} \end{vmatrix} & \begin{vmatrix} B'_{11} & B'_{12} \\ B'_{21} & B'_{22} \end{vmatrix} \end{bmatrix} \times \quad \text{Equation (68)}$$

$$\begin{bmatrix} C'_{11} & C'_{12} & C'_{13} \\ C'_{21} & C'_{22} & C'_{23} \\ C'_{31} & C'_{32} & C'_{33} \end{bmatrix} = \begin{bmatrix} D'_{11} & D'_{21} & D'_{31} \\ D'_{12} & D'_{22} & D'_{32} \\ D'_{13} & D'_{23} & D'_{33} \end{bmatrix}.$$

$D'_{3\times 3}$ matrix is converted to obtain E' matrix which is expressed by equation (69):

$$E'_{3\times 3} = D'^T_{3\times 3} = \begin{bmatrix} E'_{11} & E'_{12} & E'_{13} \\ E'_{21} & E'_{22} & E'_{23} \\ E'_{31} & E'_{32} & E'_{33} \end{bmatrix}. \quad \text{Equation (69)}$$

Accordingly, the RGB value ($O''_{RGB}$) of the output image is the product of E matrix and the RGB value ($I'_{RGB}$) of the input image, and the mathematical expression is expressed by equation (70):

$$O''_{RGB} = E'_{3\times3} \times I'_{RGB} \begin{bmatrix} R'' \\ G'' \\ B'' \end{bmatrix} = \begin{bmatrix} E'_{11} & E'_{12} & E'_{13} \\ E'_{21} & E'_{22} & E'_{23} \\ E'_{31} & E'_{32} & E'_{33} \end{bmatrix} \times \begin{bmatrix} R' \\ G' \\ B' \end{bmatrix}. \quad \text{Equation (70)}$$

Therefore, the R", G", B" values of the output image are expressed by equation (71)-equation (73):

$$R'' = E'_{11}R' + E'_{12}G' + E'_{13}B' \quad \text{Equation (71);}$$

$$G'' = E'_{21}R' + E'_{22}G' + E'_{23}B' \quad \text{Equation (72); and}$$

$$B'' = E'_{31}R' + E'_{32}G' + E'_{33}B' \quad \text{Equation (73),}$$

where $E'_{11}$-$E'_{33}$ are 9 coefficient values that required for operation of the second 3×3 color mapping_1 matrix.

Second color checker adjusted data catch_2 module 3030: the image values are placed in the captured image window 102 which is previously converted by the second 3×3 color mapping_2 matrix module 3028. The second color checker adjusted data catch_2 module 3030 is used to capture the RGB values of 16 pixels of each color blocks 501-524 in the captured image window 102, and to calculate the average values of the RGB values of 16 pixels of each color blocks 501-524 of the color checker 50. Finally, the RGB values of the image are to be captured are obtained. In the present invention, the average values of the RGB values of 16 pixels of each color blocks 501-524 is transmitted to the microprocessor 304 by the second color checker adjusted data catch_2 module 3030.

sRGB Gamma 2.2 calibration module 3032: sRGB Gamma 2.2 calibration module 3032 is used to calibrate the monitor 10 to conform with sRGB Gamma 2.2 standard, and sRGB Gamma 2.2 lookup table is transmitted to the image calibration module 302. The sRGB Gamma 2.2 lookup table is calculated as follows:
the definition of sRGB is expressed by Equation (74):

$$LUT_i = \left(\frac{i}{N-1}\right)^m \times 2^D - 1, \quad \text{Equation (74)}$$

where i=0, 1, 2, 3, ..., N−1, N is the input value of sRGB Gamma 2.2 lookup table, i is scale, m is Gamma value, and D is depth. Accordingly, in this embodiment of the present invention, Gamma value is 2.2, the input value of lookup table is 4096, and depth D is 16 bits, so the equation (74) can be rewritten as Equation (75):

$$LUT_i = \left(\frac{i}{N-1}\right)^{2.2} \times 2^D - 1. \quad \text{equation (75)}$$

Accordingly, $O'''_{RGB}$ is obtained by calculating $O''_{RGB}$ with sRGB Gamma 2.2 lookup table.

De-gamma calibration module 3036: since the monitor 10 typically includes a non-linear curve Gamma, the monitor 10 is calibrated to linear Gamma curve by De-gamma calibration module 3036, and De-Gamma lookup table is transmitted to the image calibration module 304 by the microprocessor 304.

First, the gamut mapping 3×3 coefficients are calculated, and the linear transformation formula is defined as shown in equation (76):

$$\begin{bmatrix} X \\ Y \\ Z \end{bmatrix} = M \begin{bmatrix} R \\ G \\ B \end{bmatrix} + \begin{bmatrix} X_K \\ Y_K \\ Z_K \end{bmatrix} = \begin{bmatrix} X_R & X_G & X_B \\ Y_R & Y_G & Y_B \\ Z_R & Z_G & Z_B \end{bmatrix} \begin{bmatrix} R \\ G \\ B \end{bmatrix} + \begin{bmatrix} X_K \\ Y_K \\ Z_K \end{bmatrix}, \quad \text{Equation (76)}$$

where M is the transformation matrix, R, G, B values are normalized to be between 0-1, and the equation (76) can be rewritten by equation (77)~equation (79):

$$S_R = X_R + Y_R + Z_R \quad \text{Equation (77);}$$

$$S_G = X_G + Y_G + Z_G \quad \text{Equation (78); and}$$

$$S_B = X_B + Y_B + Z_B \quad \text{Equation (79),}$$

in which above equation (77)~equation (79) can further be rewritten to obtain the equation (80):

$$\begin{bmatrix} X_W - X_K \\ Y_W - Y_K \\ Z_W - Z_K \end{bmatrix} = \begin{bmatrix} x_R & x_G & x_B \\ y_R & y_G & y_B \\ z_R & z_G & z_B \end{bmatrix} \begin{bmatrix} S_R & 0 & 0 \\ 0 & S_G & 0 \\ 0 & 0 & S_B \end{bmatrix} \begin{bmatrix} R \\ G \\ B \end{bmatrix}. \quad \text{Equation (80)}$$

Next, the white color RGB values (4096, 4096, 4096) is substituted into equation (80) to obtain equation (81):

$$\begin{bmatrix} S_R \\ S_G \\ S_B \end{bmatrix} = \begin{bmatrix} x_R & x_G & x_B \\ y_R & y_G & y_B \\ z_R & z_G & z_B \end{bmatrix}^{-1} \begin{bmatrix} X_W - X_K \\ Y_W - Y_K \\ Z_W - Z_K \end{bmatrix}, \quad \text{Equation (81)}$$

and equation (81) is further substituted into equation (76) to obtain the equation (82):

$$M = \begin{bmatrix} x_R & x_G & x_B \\ y_R & y_G & y_B \\ z_R & z_G & z_B \end{bmatrix} \begin{bmatrix} S_R & 0 & 0 \\ 0 & S_G & 0 \\ 0 & 0 & S_B \end{bmatrix}. \quad \text{Equation (82)}$$

Thus, according to the RGB specification:

$$(x_R, y_R) = (0.6391, 0.3392) \quad \text{Equation (83);}$$

$$(x_G, y_G) = (0.2718, 0.6145) \quad \text{Equation (84);}$$

$$(x_B, y_B) = (0.1453, 0.0585) \quad \text{Equation (85);}$$

$$(X_K, Y_K, Z_K) = (0, 0, 0) \quad \text{Equation (86); and}$$

$$(X_W, Y_W, Z_W) = (0.9504, 1.0, 1.0889) \quad \text{Equation (87),}$$

the equation (88) is obtained by substituting equation (83) ~equation (87) into equation (82):

$$M_{sRGB} = \begin{bmatrix} 0.4123 & 0.3576 & 0.1805 \\ 0.2126 & 0.7152 & 0.0722 \\ 0.0193 & 0.1192 & 0.9504 \end{bmatrix}. \quad \text{Equation (88)}$$

Next. R, G, B primary colors of the panel of the monitor 10 and the RGB value of whole black and whole white are measured and are substituted into equation (76) to calculate the transformation matrix $M_{panel}$ of the panel of the monitor 10:

$$\begin{bmatrix} X \\ Y \\ Z \end{bmatrix} = M_{panel} \begin{bmatrix} R_{sRGB} \\ G_{sRGB} \\ B_{sRGB} \end{bmatrix}; \quad \text{Equation (88)}$$

$$\begin{bmatrix} X \\ Y \\ Z \end{bmatrix} = M_{panel} \begin{bmatrix} R_{panel} \\ G_{panel} \\ B_{panel} \end{bmatrix}, \quad \text{Equation (89)}$$

and equation (88) and equation (89) are combined to obtain equation (91):

$$M_{panel} \begin{bmatrix} R_{sRGB} \\ G_{sRGB} \\ B_{sRGB} \end{bmatrix} = M_{panel} \begin{bmatrix} R_{panel} \\ G_{panel} \\ B_{panel} \end{bmatrix}, \quad \text{Equation (91)}$$

and equation (91) is adjusted to obtain the equation (92):

$$\begin{bmatrix} R_{sRGB} \\ G_{sRGB} \\ B_{sRGB} \end{bmatrix} = M_{sRGB}^{-1} \cdot M_{panel} \begin{bmatrix} R_{panel} \\ G_{panel} \\ B_{panel} \end{bmatrix}. \quad \text{Equation (92)}$$

Accordingly, the color conversion matrix can be obtained:

$$M_{CSC} = M_{sRGB}^{-1} \cdot M_{panel} \quad \text{Equation (93); and}$$

$$O''''_{RGB} = M_{csc} \times O'''_{RGB} \quad \text{Equation (94).}$$

In addition, the output RGB value, $O''''_{RGB}$, is calculated as follows. The De-Gamma lookup table value is calculated. The input value of the lookup table is 4096 and the depth D is 16 bits. Next, the native grayscale brightness of the panel of the monitor 10 is measured, and a brightness reference table of $2^D = 65536$ is performed by interpolation, wherein the darkest scale of the brightness is expressed by $L_{min}$ and the brightest scale of the brightness is expressed by $L_{max}$. Accordingly, the target brightness of each scale of De-Gamma lookup table can be obtained, and the formula can be expressed by equation (95):

$$L_i = (L_{max} - L_{min}) \times \frac{i}{N-1}, \quad \text{Equation (95)}$$

where, i=0, 1, 2, 3, . . . , N−1, when i=0, Li=0.

Finally, the monitor 10 displays that the image is captured by the calibrated endoscope. Herein, when the color checker 50 selection is performed, the above De-Gamma lookup table and $O''''_{RGB}$ are calculated to obtain image $O''''_{RGB}$ that is to be outputted to the monitor 10.

Flex bus 3038: one end of the flex bus 3038 is electrically connected to the microprocessor 304 and the other end of FB 3038 is electrically connected to the color checker original data catch module 3022, the first 3×3 color mapping_1 matrix module 3024, the first color checker adjusted data catch_1 module 3026, the second 3×3 color mapping_2 matrix module 3028, the second color checker adjusted data catch_2 module 3030, the sRGB Gamma 2.2 calibration module 3032, the 3×3 gamut mapping matrix module 3034, and De-gamma calibration module 3036 The flex bus 3038 is used to transmit the electrical signal which is processed by the microprocessor 304 to each module of the image calibration module 302.

Please continue to refer FIG. 3. The microprocessor 304 is used to receive the electrical signal transmitted by the optical sensor, in which the electrical signal is obtained by the light receiving surface of the optical sensor faces the center of the monitor 10. That is, the optical sensor is used to align the captured image window 102 to capture the optical signal in the captured image window 102, and then the optical signal is converted to the electrical signal by the microprocessor 304. In this embodiment of the present invention, the microprocessor 304 further includes an action controller 3042, and a calibration controller 3044, in which the action controller 3042 is used to receive the external input command, and perform the release of the action command and control the self-calibrating procedure of the image calibration device 30. Herein, the external input command is transmitted and released by using the external device (not shown) such as keyboard. When the action controller 3042 receives the external input command from the external device, the action controller 3042 will perform the release of the action command and control the self-calibrating procedure of the display correction device 30.

Moreover, the calibration controller 3044 at least includes a calculation function module 30442 and a compensate function module 30444. The calculation function module 30442 is used to calculate the electrical signal with Gamma calibration curve function operation, color temperature function operation and 3×3 gamut mapping matrix parameter operation. The purpose of the electrical signal with Gamma calibration curve function operation, color temperature function operation and 3×3 gamut mapping matrix parameter operation for the electrical signal is to let the Gamma calculation curve, color temperature and color gamut corresponding to the Gamma calibration curve, the color temperature and the color gamut of the image signal are to be outputted on the monitor 10.

The compensate function module 30444 is used to perform a uniform compensation operation and a De-Gamma calibration operation. Similarly, the above electrical signal is operated with the uniform compensation operation and De-Gamma calibration operation by the compensation function module 30444, so that the uniformity for the brightness and chromaticity of the monitor 10 are corresponding to the uniformity of the image signal of the monitor 10. At the same time, the non-linear curve of the electrical signal is calibrated to the Gamma curve which is matched to the linear Gamma curve is calibrated by the De-Gamma calibration module 3036.

According to aforementioned, for the bus transmission data, the data transmission between each module 3022-3026 of image calibration module 302, the flex bus 3036, and microprocessor 304 is further illustrated as following. The catch color checker 24 card original RGB data is obtained by the color checker original data catch module 3022 captures the RGB values of each color blocks 501-524 of the color checker 50, and the RGB values of each color blocks 501-524 of the color checker 50 is 8 bits. Because the color checker 50 includes 24 color blocks 501-524, and there are 24 RGB values. Then, 24 RGB values are transmitted to the microprocessor 304, that is, the arrow direction between the color checker original data catch module 3022 and the flex bus 3038 as shown in FIG. 3. The first color mapping_1 3×3 coefficient value is a function of the calibration controller 3044 of the microprocessor 304 to calculate the first corresponding 3×3 mapping matrix of the color checker 50. The function includes 9 values. The microprocessor 304 transmits the 9 values of the function through the flex bus 3038 to the first 3×3 color mapping_1 matrix module 3024 of the image calibration module 302. The first catch color checker 24 card adjusted_1 RGB data is a RGB data which is obtained by the first color checker adjusted data catch_1 module 3026 captures the RGB values of 24 color blocks 501-524 calculated by the first color checker adjusted data catch_1 module 3026, where the R, G, B values are each 8 bits. Therefore, the color checker includes 24 RGB values (because there are 24 color blocks 501-524), and the 24 RGB values are transmitted to the microprocessor 304 through the flex bus 3038. The second color mapping_2 3×3 coefficient values is a function of the calibration controller 3044 of the microprocessor 304 to calculate second corresponding 3×3 mapping matrix of the color checker 50. The function includes 9 values. The microprocessor 304 calculates the coefficients required for the second 3×3 color mapping_2 matrix module 3028, and the coefficients are transmitted to the second 3×3 color mapping_2 matrix module 3028 for processing. The second color adjusted RGB data is a RGB values of the 24 color blocks 501-524 of the color checker 50 calculated by the second 3×3 mapping operation that is captured by the second color checker adjusted data catch_2 module 3030, in which the RGB values of each color blocks 501-524 is 8 buts respectively. Thus, 24 RGB values are transmitted to the microprocessor 304 through the second color checker adjusted data catch_2 module 3030 of the image calibration module 302. sRGB Gamma lookup table is a Gamma 2.2 lookup table which is generated by calibrating the panel of the monitor 10 with Gamma 2.2 calibration by the calibration controller 3044, in which Gamma 2.2 lookup table includes R, G, B lookup table values. Each R, G, B lookup table values are 4096 calibration values with 12 bits. The Gamma 2.2 lookup table is transmitted to the sRGB Gamma 2.2 calibration module 3032 of the image calibration module 302 through the flex bus 3038 by the microprocessor 304, and Gamma 2.2 lookup table is stored in the sRGB Gamma 2.2 calibration module 3032. The gamut mapping 3×3 coefficient values is a color gamut of the panel of the monitor 10 which is calculated by the calibration controller 3044 of the microprocessor 304, so that the gamut mapping 3×3 coefficient values can conform to the function of the sRGB gamut standard corresponding to the 3×3 matrix. The gamut mapping 3×3 coefficient values includes 9 coefficient values. Then, 9 coefficient values are transmitted to the 3×3 gamut mapping matrix module 3034 of the image calibration module 302 through the flex bus 3038 by the microprocessor 304. The De-Gamma lookup table value is a De-Gamma table value which is generated by calibrating the panel of the monitor 10 with the De-Gamma calibration by using the calibration controller 3044 of the microprocessor 304. The De-Gamma lookup table includes R, G, B lookup table values, and each R, G, B lookup table values are 4096 calibration values with 12 bits. The De-Gamma lookup values is transmitted to the De-Gamma calibration module 3036 of the image calibration module 302 through the flex bus 3038 by the microprocessor 304. The color card calibration selection can calibrate more than one endoscope parameters, that is, the different brands and/or different models of the endoscope 20. The calibration parameters of each endoscope 20 is stored in a storage device (not shown) of the monitor 10. When the monitor 10 is connected to the endoscope 20 of the different brands, the calibration values can be directly selected from the storage device of the monitor 10 to correspond to the suitable endoscope 20.

Figure 4:
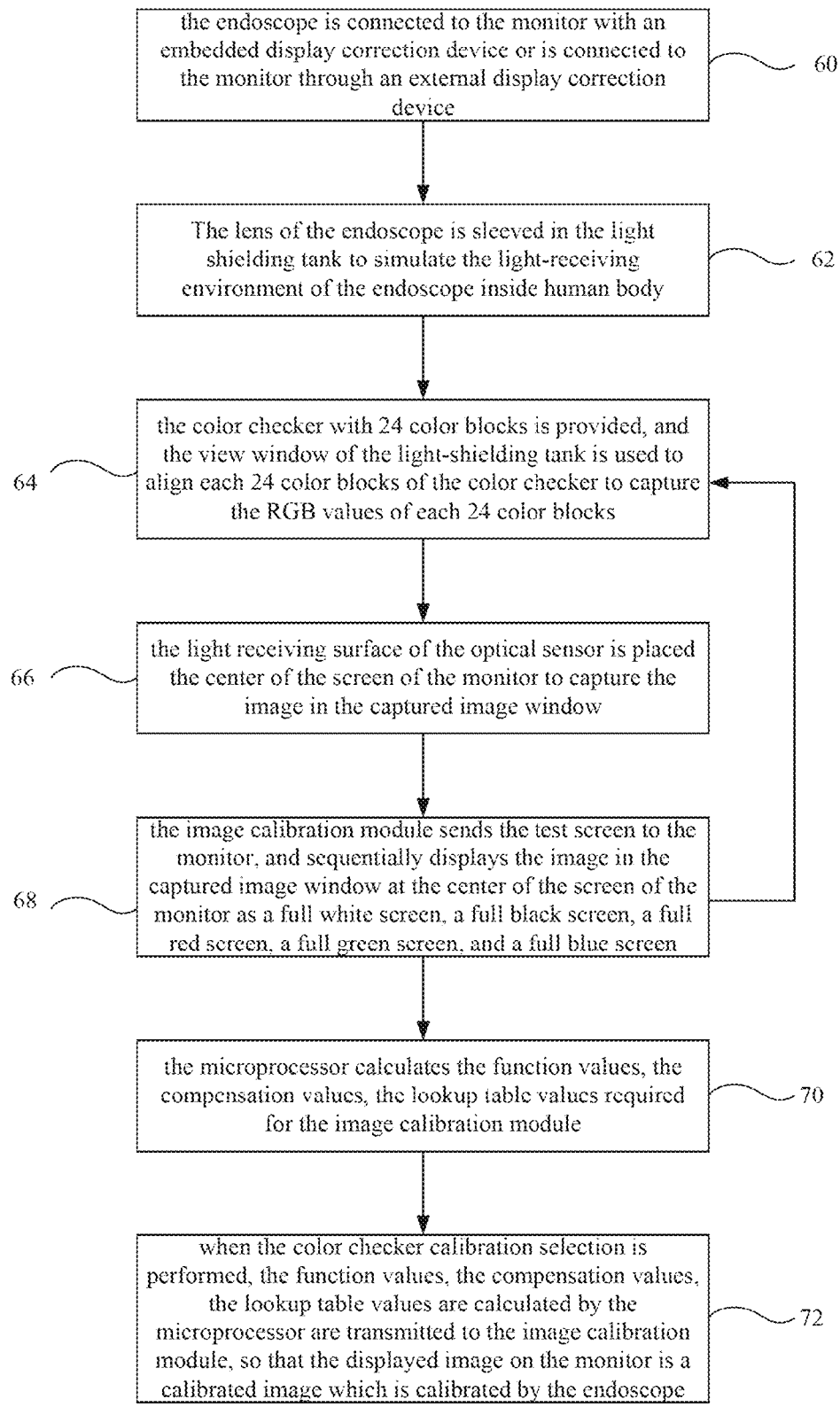
FIG. 4 is a flow chart of the correction method for the endoscope in accordance with the present invention disclosed herein.

Next, please continue to refer FIG. 4, and while stating the process flow of FIG. 4, it also cooperates with FIG. 1 and FIG. 3. In FIG. 4, step 60: the endoscope is connected to the monitor with an embedded display correction device or is connected to the monitor through an external display correction device. In this step 60, when the endoscope 20 is connected to the monitor 10, the image is captured by the lens 222 of the endoscope 20 and is displayed on the monitor 10. Next, step 62: the lens of the endoscope is sleeved in the light-shielding tank to simulate the light receiving environment of the endoscope inside human body. In this step 62: the lens 222 at one end of the insertion part 222 of the endoscope 20 is sleeved in a light-shielding tank 40 and the one end of the lens 222 to be observed the object toward the view window 404 of the light-shielding tank 40. Is should be noted that there is no light source enters into the light-shielding tank 40. The light source provided for calibrating the endoscope 20 is a self-illuminating source of the endoscope 20. So that the lens 222 of the endoscope 20 can capture the image of the object through the view window 404 of the light-shielding tank 40. It should be noted that, the object refers to the image of each color blocks 501-524 of the color checker 50, and the object observed by the general endoscope 20 refers to the lesion inside the human body.

Next, step 64: the color checker with 24 color blocks is provided, and the view window of the light-shielding tank is used to align each 24 color blocks of the color checker to capture the RGB values of each 24 color blocks. The step 64 is an execution step for the color checker calibration process. In this step 64, the light-shielding tank 40 is first placed over the color block 501 of the color checker 50, so that the monitor 10 can not only display the color block 501 of the color checker 50, but also display the related information of the color block 501 of the color checker 50. In this embodiment, the related information of the color block 501 of the color checker 50 displayed on the monitor 10 is the RGB value of the color block 501 captured by the lens 222 of the endoscope 20. For example, reference number 501 donates the first color block which refers to "dark skin" in Table 1. The first color block (dark skin) includes an R value of 115, a G value of 50 and a B value of 64, and is pressed by an external device such as keyboard (not shown). When the "enter" key of the keyboard is pressed, the message displayed on the monitor 10 to indicate to move to next color block 502. Then, the light-shielding tank e 40 includes the lens 222 of the endoscope 20 therein is moved to the color block 502. Similarly, the monitor 10 will display the image of color block 502 and capture the RGB values of the color block 502. After user pressed the "ok" button of the keyboard, the message on the screen of the monitor 10 will indicate to move next color block 503, and repeat the above steps until the RGB values of the image of the 24$^{th}$ color block 524 is captured and calculated.

In step 66: the light receiving surface of the optical sensor is placed the center of the screen of the monitor to capture the image in the captured image window. In this step 66, the light receiving surface of the optical sensor is embedded in the monitor 10 or is arranged in the display correction device 30 is placed on the captured image window 102 at the center of the screen of the monitor 10 to detect the optical signal of the 24 color blocks 501-524 of the color checker 50 captured by the endoscope 20, and the optical sensor is converted the 24 optical signals of 24 color blocks 501-524 into the 24 electrical signals.

Next, step 68: the image calibration module sends the test screen to the monitor, and sequentially displays the image in the captured image window at the center of the screen of the monitor as a full white screen, a full black screen, a full red screen, a full green screen, and a full blue screen. In this step 68, the image calibration module 302 sends the test screen to the monitor 10, so that the captured image window 102 at the center of the monitor 10 can display the image screen transmitted by the image calibration module 302. If the screen is full white screen, the RGB values of the full white screen is (4096, 4096, 4096), and at the same time, the light receiving surface of the optical sensor is conform to place in front of the captured image window 102, the image value in the captured image window 102 will be a full black screen, and the RGB values of the full black screen is (0, 0, 0) that successively increases the RGB values, so the RGB values is increased from RGB (0, 0, 0) to RGB (64, 64, 64), RGB (128, 128, 128) . . . until RGB (4096, 4096, 4096) which is 64 scale variation of white color. The 64 scale change of red color variation is from RGB (0, 0, 0), RGB (64, 0. 0). RGB (128, 0, 0) . . . until RGB (4096, 0, 0). Similarly, 64 scale variation of green color is from RGB (0, 0, 0), RGB (0, 64, 0), RGB (0, 128, 0) . . . until RGB (0, 4096, 0). 64 scale variation of blue color is from RGB (0, 0, 0), RGB (0, 0, 64), RGB (0, 0, 128) . . . until RGB (0, 0, 4096), and repeat the above step 64 to step 68 until the measurement of each color block 501-524 of the color checker 50 is completed to complete the calibration process of the endoscope 20.

Next, step 70: the microprocessor calculates the function values, the compensation values, the lookup table values required for the image calibration module. In this step 70, the calibration controller 3044 of the microprocessor 304 calculates the coefficient values of first 3×3 color mapping_1 matrix, the coefficient values of second 3×3 color mapping_1 matrix, sRGB Gamma lookup table, the coefficient values of 3×3 gamut mapping matrix and the De-Gamma lookup table.

In step 72: when the color checker calibration selection is performed, the function values, the compensation values, the lookup table values are calculated by the microprocessor are transmitted to the image calibration module, so that the displayed image on the monitor is a calibrated image which is calibrated by the endoscope.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A display correction system applied for an endoscope, comprising: a color checker, the color checker is composed of 24 various color blocks;
    a light-shielding tank, the light-shielding tank is a cylinder shape, a through hole is on a first surface of the light-shielding tank and a view window is on a second surface of the light-shielding tank, wherein the through hole is communicated with the view window;
    the endoscope used in observing internal organs of a human body, the endoscope includes an insertion part and a controlling part, and the insertion part is connected to the controlling part, wherein one end of the insertion part includes a lens which is sleeved in the through hole, and the lens is set toward to the view window, and one end of the controlling part includes an image signal connection terminal, wherein the lens is sleeved in the light-shielding tank that aligned each color block of the color checker to capture an image of each color block;
    a monitor, the monitor includes a captured image window that is provided for displaying each image of the each color block; and
    a display correction device, the display correction device includes an image calibration module which is provided for calibrating each image signal of each color block transmitted from the endoscope, wherein the image calibration module further comprises:
        an image input terminal, the image input terminal is provided for receiving each image signal of each image of each color block which is captured by the lens of the endoscope;
        a microprocessor, the microprocessor is provided for receiving an electrical signal corresponding to each image signal and calculating and calibrating the electrical signal; and
        an image output terminal, the image output terminal is provided for connecting to the monitor, the electrical signal after calibrating and calculating by the microprocessor and then is outputted to the monitor through the image output terminal, so that color of each image corresponding to each electrical signal displayed on the monitor is the same as a true color of each color block.

2. The display correction system applied for the endoscope according to claim 1, wherein the light-shielding cartridge is a black light-shielding cartridge.

3. The display correction system applied for an endoscope according to claim 1, wherein the endoscope can be a cystoscopy, a gastroscopy, a colonoscopy, a bronchoscope or a laparoscope.

4. The display correction system applied for an endoscope according to claim 1, wherein the microprocessor at least includes an action controller, a calibration controller, a calculation function unit, and a compensation function unit.

5. The display correction system applied for an endoscope according to claim 4, wherein the action controller is provided for receiving a user's keyboard operation, an action command, and a control automatic self-calibrating process sequence.

6. The display correction system applied for an endoscope according to claim 4, wherein the calculation function unit is provided for calculating the electrical signal with a Gamma calibration curve function operation, a color checker function operation, and a 3×3 gamut mapping matrix operation.

7. The display correction system applied for an endoscope according to claim 4, wherein the compensation function unit is provided for operating the electrical signal with a luminance and chrominance uniform compensation function operation and a De-Gamma calibration operation.

8. The display correction system applied for an endoscope according to claim 1, wherein the electrical signal is converted from an optical signal which is detected by an optical sensor having a light-receiving surface aligned with the captured image window of the monitor.

9. The display correction system applied for an endoscope according to claim 8, wherein the optical sensor is embedded in the monitor or is embedded in the display correction device.

10. The display correction system applied for an endoscope according to claim 8, wherein the optical sensor is further provided for aligning the captured image window on the monitor to capture each image signal of each image of each color block.

11. The display correction system applied for an endoscope according to claim 10, wherein the optical sensor is embedded in the monitor or is embedded in the display correction device.

* * * * *